(12) United States Patent
Amir et al.

(10) Patent No.: US 11,858,887 B2
(45) Date of Patent: Jan. 2, 2024

(54) LINKER COMPOUNDS, METHODS OF PRODUCING THE SAME AND USES THEREOF

(71) Applicant: Shenkar College of Engineering and Design, Ramat Gan (IL)

(72) Inventors: Elizabeth Amir, Tel Aviv (IL); Daniel Anavi, Ramat Hasharon (IL)

(73) Assignee: Shenkar College of Engineering and Design, Ramat Gan (IL)

( * ) Notice: Subject to any disclaimer, the term of this patent is extended or adjusted under 35 U.S.C. 154(b) by 0 days.

(21) Appl. No.: 16/496,920

(22) PCT Filed: Mar. 21, 2018

(86) PCT No.: PCT/IL2018/050326
§ 371 (c)(1),
(2) Date: Sep. 23, 2019

(87) PCT Pub. No.: WO2018/173057
PCT Pub. Date: Sep. 27, 2018

(65) Prior Publication Data
US 2020/0087238 A1     Mar. 19, 2020

(30) Foreign Application Priority Data
Mar. 21, 2017 (IL) ......................... 251323

(51) Int. Cl.
*C08B 3/08* (2006.01)
*C08B 3/14* (2006.01)
(Continued)

(52) U.S. Cl.
CPC .............. *C07C 57/03* (2013.01); *C07C 21/02* (2013.01); *C07C 21/22* (2013.01); *C07C 33/02* (2013.01);
(Continued)

(58) Field of Classification Search
CPC ......... C07C 57/18; C07C 57/03; C07C 33/02; C07C 33/04; C07C 33/048; C07C 21/22;
(Continued)

(56) References Cited

U.S. PATENT DOCUMENTS 8,299,200 B2   10/2012   Webster et al.
2016/0208087 A1   7/2016   Virtanen et al.

FOREIGN PATENT DOCUMENTS

WO   WO 99/49124   9/1999
WO   WO 2007/125429   11/2007
(Continued)

OTHER PUBLICATIONS

Zhao et al., "Heterogeneous "Organoclick" Derivatization of Polysaccharides: Photochemical Thiol-ene Click Modification of Solid Cellulose" Macromol Rapid Commun vol. 31 pp. 740-744 (Year: 2010).*

(Continued)

*Primary Examiner* — Eric Olson
(74) *Attorney, Agent, or Firm* — GREENBERG TRAURIG, LLP (57) ABSTRACT

The present disclosure provides a bifunctional linker for coupling at least one functional moiety, preferably a bis-allyl propionic acid (BAPA), to a polymer-containing matrix. Also disclosed by the present disclosure are anhydrides of the bifunctional linker, processes for preparing the bifunctional linker and such anhydride, as well as surfaces, such as cellulose containing matrices, coupled with the bifunctional linker, at times, the latter carrying a functional agent.

12 Claims, 6 Drawing Sheets

(51) Int. Cl.
| | |
|---|---|
| C07C 57/03 | (2006.01) |
| C07C 321/04 | (2006.01) |
| C07D 303/18 | (2006.01) |
| C07C 21/02 | (2006.01) |
| C07D 303/22 | (2006.01) |
| C07C 57/18 | (2006.01) |
| C07C 33/048 | (2006.01) |
| C07C 33/02 | (2006.01) |
| C07C 21/22 | (2006.01) |
| C07C 33/04 | (2006.01) |
| C08B 15/00 | (2006.01) |
| C07C 67/14 | (2006.01) |
| C07C 57/68 | (2006.01) |
| C07C 57/66 | (2006.01) |
| C07C 67/08 | (2006.01) |

(52) U.S. Cl.
CPC ............ *C07C 33/04* (2013.01); *C07C 33/048* (2013.01); *C07C 57/18* (2013.01); *C07C 57/66* (2013.01); *C07C 57/68* (2013.01); *C07C 67/08* (2013.01); *C07C 67/14* (2013.01); *C07C 321/04* (2013.01); *C07D 303/18* (2013.01); *C07D 303/22* (2013.01); *C08B 3/08* (2013.01); *C08B 3/14* (2013.01); *C08B 15/00* (2013.01)

(58) Field of Classification Search
CPC ..... C07C 21/02; C07C 321/08; C07D 303/22; C08B 15/00; C08B 3/08
See application file for complete search history.

(56) References Cited

FOREIGN PATENT DOCUMENTS

| WO | WO 2011/090428 | 7/2011 |
|---|---|---|
| WO | WO 2012/005648 | 1/2012 |
| WO | WO 2012/120198 | 9/2012 |

OTHER PUBLICATIONS

Kvasnica, "Dicyclohexylcarbodiimide (DCC)" Synlett No. 14 pp. 2306-2307 (Year: 2007).*

Montanez et al., "Bifunctional Dendronized Cellulose Surfaces as Biosensors" Biomacromolecules vol. 12 pp. 2114-2125 (Year: 2011).*

Campos et al., "Click chemistry strategies for the fabrication of dendrimers" PMSE Preprints CODEN: PPMRA9; ISSN: 1550-6703, http://pubs.acs.org/cgi-bin/preprints/display?div=pmse&meet=239&page=13064_21682.pdf, 2 pages (Year: 2010).*

Carlmark et al., "Dendritic architectures based on bis-MPA: functional polymeric scaffolds for application-driven research," Chem Soc Rev 2013 vol. 42 pp. 5858-5879 DOI: 10.1039/c3cs60101c (Year: 2013).*

Yang et al., "Synthesis and characterization of cellulose fibers grafted with hyperbranched poly(3-methyl-3-oxetanemethanol)" Cellulose vol. 18 pp. 1611-1621 DOI 10.1007/s10570-011-9587-y (Year: 2011).*

E. Ostmark et al., "Dendritic Structures Bases on Bis (Hydroxymethyl) propionic Acid as Platforms for Surface Reactions," 2005, Langmuir, vol. 21, No. 10, p. 4512-4519.

E. Ostmark et al., Dendronized Hydroxypropyl Cellulose: Synthesis and Characterization of Biobased Nanoobjects, Oct. 2, 2007, Biomacromecules, vol. 8, No. 12, p. 3815-3822.

K. Olofsson et al., Soft hydrogels from tetra-functional PEGs using UV-induced thiol-ene coupling chemistry: a structure-to-property study, Jul. 11, 2014, RSC Advances, p. 30119-30120.

L. M. Campos et al., Click Chemistry Strategies for the Fabrication of Dendrimers, Dec. 31, 2010, Proceedings of the American Chemical Society.

P Antoni et al., Pushing the Limits for Thiol-Ene and CuAAC Reactions Synthesis of a 6$^{th}$ Generation Dendrimer in a Single Day, Jun. 26, 2010, Macromolecules, vol. 43, No. 16, 2010, p. 6625-6631.

Zheng Zhang, Modification chimique de la cellulose nanofibrille par les alcoxysilanes; University Sciences et Technologies, p. 23-25, Feb. 26, 2014.

L. Wang et al., "Click" Synthesis of Instrnsically Hydrohollic Dendrons and Dendrimers Containing Metal Binding Moieties at Each Branching Unit, Mar. 17, 2014, Macromolecules, vol. 39, p. 2199-2213.

K. Missoum et al., Nanofibrillated Cellulose Surface Modification: A Review, May 3, 2013, Material, vol. 6, p. 1745-1766.

J. D'Amour KT et al., Synthesis of novel types of polyester glycodendrimers as potential inhibitors of urinary tract infections, Mar. 19, 2015, New Journal of Chemistry, vol. 39, p. 4115-4127.

Patent Cooperation Treaty International Searching Authority, International Search Report and Written Opinion, dated May 6, 2018, 11 pages, PCT/IL2018/050326, Israel Patent Office, Malcha Jerusalem.

Registry Copyright 2020 ACS on STN, RN 271790-78-4, Entered STN: Jun. 21, 2000.

* cited by examiner

LINKER COMPOUNDS, METHODS OF PRODUCING THE SAME AND USES THEREOF

CROSS-REFERENCE TO RELATED APPLICATIONS

This application is a United States national stage application under 35 U.S.C. § 371 of PCT Application No. PCT/IL2018/050326 designating the United States, filed on Mar. 21, 2018, which is hereby incorporated by reference in its entirety and which claims priority to Israeli Patent App. No. 251323, filed on Mar. 21, 2017.

TECHNOLOGICAL FIELD

The present disclosure relates to bifunctional linkers and their use in matrices functionalization.

BACKGROUND ART

References considered to be relevant as background to the presently disclosed subject matter are listed below:
- International patent application publication No. WO 12/120198.
- International patent application publication No. WO 2011/090428.
- International patent application publication No. WO 99/49124.
- Emma Östmark et al. "Dendritic Structures Based on Bis(hydroxymethyl)propionic Acid as Platforms for Surface Reactions" Langmuir 2005, 21, 4512-4519
- Emma Östmark et al. "Dendronized Hydroxypropyl Cellulose. Synthesis and Characterization of Biobased Nanoobjects" Biomacromolecules 2007, 8, 3815-3822.

Acknowledgement of the above references herein is not to be inferred as meaning that these are in any way relevant to the patentability of the presently disclosed subject matter.

BACKGROUND

Cellulose, being regarded as one of the most important renewable organic raw material, is widely used in various industries. Yet, for improved performance, there is an ongoing need to improve its reactivity and compatibility with other materials. To this end, techniques for modifying are continuously under development.

International patent application publication No. WO 12/120198 describes a method of modifying the surface of a cellulosic material, as well as an intermediate product of said method. Specifically, WO12/120198 makes use of the click chemistry to modify cellulosic materials in aqueous media.

In addition, international patent application publication No. WO 2011/090428 describes the use of thiol-ene "click chemistry" to modify polysaccharide-based material.

International patent application publication No. WO 99/49124 describes a method of modifying textile by attaching a multifunctional co-polymer containing hydrophobic and hydrophilic group that is capable of imparting fibrous and other substances with a water and oil repellency.

Emma Östmark et al. (2005) described the self-assembly of different generations of disulfide-cored 2,2-bis(hydroxymethyl)propionic acid-based dendritic structures onto gold surfaces.

Later, Emma Östmark et al. (2005) described the synthesis of dendronized polymers containing a cellulose backbone. The resulting complex material is described to provide versatile functionalization possibilities to the high molecular weight complex. The dendronized polymers were built by attaching premade acetonide-protected 2,2-bis(methylol) propionic acid functional dendrons of generation one to three to a hydroxypropyl cellulose backbone.

GENERAL DESCRIPTION

The present disclosure provides, in accordance with a first of its aspects a compound having the following formula (I):

(I)

wherein
$R_1$ and $R_2$ may be the same or different and represent a group selected from vinyl, alkyl vinyl, propargyl, alkyl propagyl, allenyl, alkyl allenyl, alkylthio and alkyl azide;
$R_3$ is a alkyl;
$X_1$ and $X_2$ may be the same or different and each is selected from the group consisting of —O—$(CH_2)_n$ or —S—$(CH_2)_n$, where n is independently with respect to $X_1$ and $X_2$ an integer from 1 to 4; and
W is a group selected from —OH, —SH, halo, epoxy and —$OR_4$ where $R_4$ is a alkyl; and
$R_5$ is selected from the group consisting of alkylene and carbonyl; or $R_5$ is a valence bond;
said compound is for use as a bifunctional linker for coupling at least one functional moiety to a polymer-containing matrix.

In accordance with a further aspect, the present disclosure provides an anhydride of a compound having a general formula (II):

(II)

wherein
$R_1$ and $R_2$ represent a group selected from vinyl, alkyl vinyl, propargyl, alkyl propagyl, allenyl, alkyl allenyl, alkylthio and alkyl azide;
$R_3$ is a alkyl;
$R_5$ is selected from the group consisting of alkylene and a carbonyl; or $R_5$ is a valence bond; and
W' is O
$X_1$ and $X_2$ may be the same or different and each is selected from the group consisting of —O—$(CH_2)_n$ or —S—$(CH_2)_n$, where n is independently with respect to $X_1$ and $X_2$ an integer from 1 to 4.

Also provided by the present disclosure, in accordance with a further aspect, is a process for preparing a compound of formula (I), as defined hereinabove and below, the process comprises reacting a propionic acid derivative of formula (IV):

(IV)

where $X_1$, $X_2$, and $R_3$ are as defined, with a nucleophile agent of the formula A-R$_1$ or A-R$_2$ wherein A is a leaving group.

In yet another aspect, there is provided by the present disclosure a process for preparing an anhydride of the formula (III):

wherein
- $R_1$ and $R_2$ represent a group selected from vinyl, alkyl vinyl, propargyl, alkyl propagyl, allenyl, alkyl allenyl, alkylthio and alkyl azide;
- $R_3$ is a alkyl;
- $X_1$ and $X_2$ may be the same or different and each is selected from the group consisting of —O—(CH$_2$)$_n$ or —S—(CH$_2$)$_n$, where n is independently with respect to $X_1$ and $X_2$ an integer from 1 to 4,
- the process comprises reacting a compound of formula (I), as defined hereinabove and below, with N,N'-Dicyclohexylcarbodiimide in the presence of a polar aprotic organic solvent.

The present disclosure also provides a modified polymer-containing matrix comprising, bound to a surface of the polymer-containing matrix a compound of formula (I) as defined hereinabove and below.

In this connection, there is also disclosed herein a process for modifying a polymer-containing matrix, the process comprises providing a polymer containing matrix having exposed polar groups; and reacting said polymer-containing matrix with an anhydride of a compound of formula (I) as defined hereinabove and below, in the presence of a reaction medium comprising an amine containing organic compound in a polar aprotic solvent, said reaction is for a time sufficient to allow the binding of said compound of formula (I) to said matrix.

In addition, provided herein is a functionalized polymer-containing matrix comprising at least one functional agent bound, via a compound of formula (I) to the polymer containing matrix.

Finally, provided herein is a modified cellulose-containing matrix comprising covalently bound to its cellulose fibers bis-allyl propionic acid (BAPA) as well as a functionalized cellulose containing matrix comprising covalently bound, via a bis-allyl propionic acid (BAPA) linker at least one functional agent.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The present disclosure is based on the development of simple, short reaction time (5 hours or less) and effective method for producing a modified cellulose-based materials, such as cellulosic fabric, cardboard and others that comprises, chemically bound thereto, via a specially developed group of bifunctional linkers, one or more functional agents. The binding of such functional agents were shown to provide the cellulose fabric with, inter alia, higher durability and strength upon long term use.

For example, one type of modification of a cellulose-based (comprising) fabric provided the fabric with an improved aesthetic finish/look and feel. An improved finish of a cellulosic matrix can be classified as a functional finish, e.g. dyeing, waterproof finish, flame-retardant finish, anti-moth finish, antistatic finish, antimicrobial, antibacterial, electro-conductive. In some other modifications, the modification provided the fabric with improved performance, namely, an improved function, e.g. smoothness, stability/durability etc.

The modification of the cellulosic fabric, as well as other polymeric matrices, is achieved by the use of a bifunctional linker.

Thus, in accordance with a first of its aspects, the present disclosure provides a bifunctional linker compound having the following general formula (I):

(I)

wherein
$R_1$ and $R_2$ may be the same or different and represent a group selected from vinyl, alkyl vinyl, propargyl, alkyl propagyl, allenyl, alkyl allenyl, alkylthio and alkyl azide;
$R_3$ is a alkyl;
$X_1$ and $X_2$ may be the same or different and each is selected from the group consisting of —O—$(CH_2)_n$ or —S—$(CH_2)_n$, where n is independently with respect to $X_1$ and $X_2$ an integer from 1 to 4;
W is a group selected from —OH, —SH, halo, epoxy, and —$OR_4$ where $R_4$ is a alkyl; and
$R_5$ is selected from the group consisting of alkylene and a carbonyl or $R_5$ is a valence bond;
said compound is for use as a bifunctional linker for coupling at least one functional moiety to a polymer containing matrix.

In some embodiments, $R_1$ is different from $R_2$.
In some embodiments, $R_1$ and $R_2$ are identical.
In some embodiments, $R_1$ and $R_2$, being the same or different, can each comprise a short chain carbohydrate. In the context of the present when referring to a short chain carbohydrate it is to be understood as meaning any chain, saturated or unsaturated carbohydrate, comprising from one or two carbon atom (depending on the type of the group) and not more than 20 carbon atoms, at times, not more than 18, or even not more than 16 carbon atoms. In some embodiments, the short chain carbohydrate comprise 2 carbon atoms, at times, 3 carbon atoms, 4, 5, 6, 7, 8, 9, 10, 11 or even up to 12 carbon atoms.

In some embodiments, $R_1$ and $R_2$ are independently selected from the group consisting of vinyl, $C_3$-$C_{12}$ alkyl vinyl, propargyl, $C_3$-$C_{12}$ alkyl propargyl, $C_3$-$C_{12}$ allenyl, $C_4$-$C_{12}$ alkyl allenyl, $C_1$-$C_{12}$ alkylthio and $C_1$-$C_{12}$ alkyl azide.

In some embodiments, $R_1$ is $C_3$-$C_{12}$ alkyl vinyl (i.e. containing at least one double bond that is terminal to the carbohydrate (alkyl) chain). In some embodiments, $R_1$ is an alkyl vinyl (e.g. allyl). In some embodiments, $R_1$ is an allyl.

In some embodiments, $R_1$ is $C_3$-$C_{12}$ a propargyl (i.e. containing at least one triple bond terminal to the carbohydrate chain).

In some embodiments, $R_1$ is $C_1$-$C_{12}$ alkylthio.
In some embodiments, $R_1$ is $C_1$-$C_{12}$ alkyl azide.
In some embodiments, $R_2$ is $C_3$-$C_{12}$ alkyl vinyl (i.e. containing at least one double bond that is terminal to the carbohydrate (alkyl) chain). In some embodiments, $R_2$ is an allyl.

In some embodiments, $R_2$ is $C_3$-$C_{12}$ a propargyl (i.e. containing at least one triple bond terminal to the carbohydrate chain).

In some embodiments, $R_2$ is $C_1$-$C_{12}$ alkylthio.
In some embodiments, $R_2$ is $C_1$-$C_{12}$ alkyl azide.
In some embodiments, $R_1$ and $R_2$ are the same and represent —$C_1$-$C_4$-vinyl, preferably, —$CH_2$—CH=$CH_2$.
In some embodiments, $R_3$ is a short alkyl chain. In some embodiments, $R_3$ is $C_1$-$C_4$ alkyl.

In some embodiments, $R_3$ is selected from a methyl, an ethyl or propyl group. Preferably, $R_3$ is a methyl group.
In some embodiments, $X_1$ is —O—$(CH_2)_n$—, when n is an integer of any one of 1, 2, 3 or 4. In some embodiments, n is 1 or 2. In on preferred embodiment, $X_1$ is —O—$CH_2$—.
In some embodiments, $X_2$ is —O—$(CH_2)_n$—, when n is an integer of any one of 1, 2, 3 or 4. In some embodiments, n is 1 or 2. In on preferred embodiment, $X_2$ is —O—$CH_2$—.
In some embodiments, $R_5$ is a carbonyl group.
In some embodiments, when said $R_5$ is a carbonyl group, W represents —OH or —Cl, preferably —OH.
In some specific embodiments, compound of formula (I) is bis-allyl propionic acid (known also by the abbreviated name BAPA) and has the structure represented by formula (IA):

(IA)

In some embodiments, $R_5$ is an alkylene, preferably $C_1$-$C_5$ alkylene.
In some embodiments, $R_5$ is selected from the group consisting of methylene or ethylene.
In some embodiments, $R_5$ is a valence bond.
In some embodiments, when $R_5$ is a valence bond, W is an epoxy.
In some specific embodiments, the compound of formula (I) is epoxy BAPA, and has the specific structure represented by formula (IB):

(IB)

The compound of formula (I) is used as a bifunctional linker for coupling at least one functional moiety to a polymer-containing matrix.

When referring to a bifunctional linker it is to be understood as a compound that provides a chemical connection between two different entities, at least one of the entities being the polymer-containing matrix. The linker is thus, in the context of the present disclosure, one that can chemically bind, on its one end to the polymer-containing matrix (e.g. to the surface of the polymer-containing matrix), and on its other end, to one or more functional moieties. In the context of the present disclosure, the binding of the at least one functional moiety is via at least one of the $R_1$ and $R_2$ groups and the binding of the linker to the polymer-containing matrix is via the W group.

In the context of the present disclosure, when referring to a chemical bond it is to be understood as encompassing a covalent bond. In some embodiments, the chemical bond is a covalent bond.

As noted above, the linker binds via its one end to a polymer containing matrix. In the context of the present disclosure, when referring to such polymeric matrix it is to be understood as matrix (structure) comprising a single type of polymer (i.e. homopolymer) or plurality of polymers, e.g. co-polymer, the matrix/structure comprising surface exposed reactive groups to which the linker binds. In the context of the present disclosure the term "reactive groups" it is to be understood as encompassing polar groups, capable of covalently binding to the linker. Such reactive groups may include, without being limited thereto, hydroxyl, carbonyl, carboxyl, amino, thiol alkyne, alkene, epoxide. In some embodiments, the exposed reactive moieties comprise a hydroxyl group.

In some embodiments, the polymer-containing matrix is one comprising an organic/natural polymer(s).

In some embodiments, the polymer-containing matrix is one comprising a synthetic polymer(s) or semi synthetic polymer(s).

In some embodiments, the polymer-containing matrix comprises a combination of organic and synthetic polymers.

In some embodiments, the polymer-containing matrix comprises plant-derived polymers.

In some embodiments, the polymer-containing matrix comprises polysaccharides.

In some embodiments, the polysaccharide is selected from the group consisting of cellulose, hemi-cellulose and lignin.

In some embodiments, the polymer-containing matrix comprises cellulose or modified cellulose. In some embodiments, the polymer-containing matrix comprises or consists essentially of cellulosic polymers.

In some other embodiments, the polymer-containing matrix comprises any one or combination of a material selected from the group consisting of viscose, wool, silk, rayon, cellophane. Each of said polymeric materials contain one or more functional groups that can be covalently linked to the bifunctional linker disclosed herein.

In some embodiments, the polymer-containing matrix comprises synthetic polymers. In some embodiments, the plastic comprises any one or combination of polyethylene, polypropylene, polyamides, polyurethanes and polyesters.

In some embodiments, cellulose (or other polymer that can bind to the bifunctional linker) can be added to a polymer containing matrix (that has no functional groups to link to the bifunctional linker) as an additive, e.g. to allow the linking of the bifunctional linker to the matrix's surface.

In some embodiments, the polymer-containing matrix comprises semi-synthetic polymers. When referring to semi-synthetic polymers it is to be understood as encompassing at least one naturally occurring polymer that has been treated/ modified to carry reactive groups for covalent attachment therethrough to the linker. In some embodiments, the semi-synthetic polymer is cellulose acetate.

In some embodiments, the polymer-containing matrix comprises polymeric fibers. In the context of the present disclosure, when referring to a matrix comprising fibers, it is to be understood as encompassing any type of fibers, including, without being limited thereto, microbifers, co-extruded fibers, fibrilsall collectively referred to herein by the term fibers.

In some embodiments, the polymer-containing matrix comprises woven, non-woven or a combination of woven and non-woven fibers.

In some embodiments, the polymer-containing matrix comprises woven fibers.

In some embodiments, the polymer-containing matrix comprises woven cellulose-containing fibers.

In some embodiments, the polymer-containing matrix is a woven cellulose containing fabric.

In some embodiments, the polymer-containing matrix comprises cotton fibers.

In some embodiments, the polymer-containing matrix is a cotton fabric.

In some embodiments, the polymer-containing matrix is a fabric as used in the textile industry.

In some embodiments, the polymer-containing matrix comprises nonwoven fibers. This may be a fabric-like material (nonwoven fibers) where the fibers (typically long fibers) are bonded together by chemical, mechanical, heat and/or solvent treatment, or any other treatment that is neither woven nor knitted.

In some embodiments, the polymer-containing matrix comprise nonwoven fibers, e.g. of a kind used in the medical industry or in the disposable products industry. Without being limited thereto, fabric-like material comprising non-woven fibers may include disposable non-woven sheets, e.g. used in disposable gowns, gloves, drapes and covers; masks; scrub suits; caps; shoe covers; bath wipes; wound dressings etc.

The polymer-containing matrix is modified with a functional moiety (via the bifunctional linker) to improve the characteristics of the matrix. The term "functional moiety" means, in the context of the present disclosure, any chemical entity/compound that attributes to at least the surface of the polymer-containing matrix a new feature/functional characteristic. In some embodiments, the functional moiety provides the matrix with higher durability and/or strength and/or stability/resistance to external damaging effects.

In some embodiments, the functional moieties is of a kind that provided the polymer-containing matrix with an improved aesthetic finish/look and feel. An improved finish of a matrix can be classified as a functional finish, e.g. any one of dyeing, waterproof finish (water proof agent), flame-retardant finish (flame retardant), anti-moth finish (anti-moth agent), antistatic finish (antistatic agent), antimicrobial (e.g. antibacterial agent), electro-conductive (electro-conducting material), texture modifying agent (an agent improving textile finish and resilience to treatments), moist-preserving agents, thermal isolating agents, thermal reflective agents, patterning agents (e.g. agents for photo-mask-selective UV passage), an agent adapted for dry finishes treatments such as brushing, calendaring, laminating, embossing, heat setting, polishing and laser treatment; each constituting an independent embodiment of the present disclosure. In some other embodiments, the functional moieties provide the matrix with improved performance, e.g. an improved function, e.g. smoothness, stability/durability, texture etc.

In some embodiments, the functional moiety is selected from the group of moieties known to be used in the textile industry.

In some embodiments the functional moieties are at least as one of a dye or reactive dye, or a dye enhancer.

Reactive dyes are to be understood as dyes that include a functional group through which fixation to the linker is made. Reactive dyes are categorized by functional group and include, for example, groups such as monochlorotirazine, monofluorochlorotriazine, dichlorotriazine, difluorochloropyrimidine, dichloroquinoxaline, trichloropyrimidine, or groups such as vinylsulfone and vinyl amide.

In some embodiments the functional moiety is a softening agent. Examples of softening agents are those typically used in the textile industry.

In some embodiments the functional moiety is an anti-delamination agent. Examples of anti-delamination agent are those typically used in the textile industry.

In some embodiments the functional moiety is an anti-microbial agent. Antimicrobials are protective agents that, being bacteriostatic, bactericidal, fungistatic and fungicidal, also offer special protection against the various forms of material rotting, e.g. textile rotting. An example of an antimicrobial agents that can be used for modification of the polymer-containing matrix include, without being limited thereto, is Triclosan (2,4,4-hydrophenyl trichloro (II) ether), a member of the antiseptic and disinfectant family.

In some embodiments the functional moiety is a fluorescent pigment. Examples of fluorescent pigments are those typically used in the textile industry, such as, without being limited thereto, coumarin dyes.

In some embodiments the functional moiety is an electro-conductive agent. Examples of electro-conductive agent that can be used, without being limited thereto, comprise organic polymers selected from polythiophenes, polypyrroles, polyanilines and their derivatives, or any combination thereof.

In some embodiments the functional moiety comprises quantum dots (semiconductor nanocrystals). In some embodiments the quantum dots comprise organic quantum dots such as, without being limited thereto, coal derived quantum dots.

In some embodiments, the bifunctional linker is linked to the polymer-containing matrix in a reaction involving an anhydride form thereof.

Thus, also provided by the present disclosure is an anhydride form of the bifunctional linker of formula (II):

where $R_1$, $R_2$, $R_3$, $R_5$, $X_1$, and $X_2$ have the meaning as defined with respect to the compound of formula (I) and W' is O.

In some embodiments, the anhydride is represented by general formula (III):

where $R_1$, $R_2$, $R_3$, $X_1$, and $X_2$ have the meaning as defined with respect to the compound of formula (I).

Compound (II) or (III) are an anhydride of the bifunctional linker of formula (I). Thus, the same definitions and embodiments provided above with respect to compound of formula (I) apply also to the anhydride of formula (II) or (III), mutatis mutandis.

In one preferred embodiment, the anhydride is a bis-allyl propionic acid (BAPA) anhydride.

The present disclosure also provides processes for the preparation of the bifunctional linker of formula (I) and for the preparation of the anhydride of formula (II) or (III).

With respect to the preparation of the bifunctional linker of formula (I), the process comprises reacting a starting compound (a propionic acid derivative) of formula (IV):

where $X_1$, $X_2$ and $R_3$ are as defined with respect to formula (I), with a nucleophilic reagent containing $R_1$ and/or $R_2$ and a leaving group.

In some embodiments, compound of formula (IV) is used for the preparation of the bifunctional linker of formula (I) where $R_1$ and $R_2$ are identical (i.e. the same nucleophilic reagent is used for both substitutions).

Yet, in some other embodiments, $R_1$ and $R_2$ can be different, this being achieved, for example, by carrying out protection of one of the hydroxyl groups of compound of Formula (V) using one equivalent of a protecting group and separating the mixture of products. Once one of the hydroxyl groups is protected, functionalization with a nucleophilic reagent of the unprotected hydroxyl, followed by de-protection and reaction of the second hydroxyl with a different nucleophilic reagent.

When referring to a leaving group in the context of the present disclosure it is to be understood as meaning a leaving group known or suitable for use in a nucleophilic substitution reaction ($SN_1$ and/or $SN_2$). Non-limiting examples of a leaving group include halides, tosylate and mesylate. In some embodiments, the leaving group is a bromide.

Figure 1A:
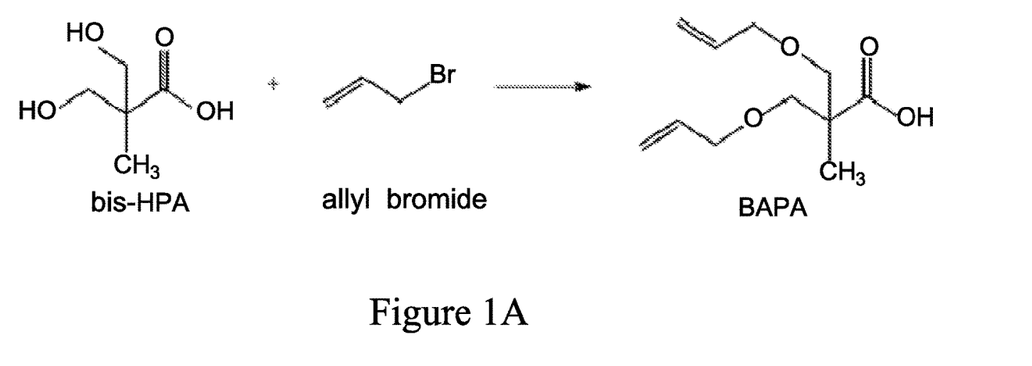
FIGS. 1A-1C are schemes describing synthesis procedures of bis-allyl propionic acid (BAPA) (FIG. 1A), BAPA anhydride: bis(allyl propionic acid) anhydride (FIG. 1B) and BAPA acyl chloride: bis(allyl propionyl chloride) (FIG. 1C)

The formation of the bifunctional linker is known in the art and is also illustrated in Figure JA, e.g. when bis-allyl propionic acid (BAPA) is formed by the use of allyl bromide.

In some embodiments, the nucleophilic substitution taking place in the preparation of the compound of formula (I) requires elevated temperatures. In some embodiments, the reaction is at a temperature of between 100° C. to 180° C., at times between 120° C. to 160° C. The temperature will be determined based on the type of nucleophile used in the reaction.

In some embodiments, the starting compound of formula (IV) is allowed to react with the nucleophilic reagent for at least one minute, at times, for at least 1, 2, 5, 10, 15, 30 or even 40 minutes and at times for more than an hour. The end of the reaction can be determined by techniques known in the art, depending on the functional agent.

For the purpose of modifying the surface of the polymer containing matrix, the bifunctional linker of formula (I) needs to first be converted to its anhydride form.

The present disclosure also provides a method of preparing an anhydride of the compound of formula (I). The anhydride form is represented by the general formula (II):

(II)

wherein $R_1$, $R_2$, $R_3$, $R_5$ $X_1$, $X_2$, $X_3$, and W' have the meaning as defined above with respect to the bifunctional linker/compound of formula (I).

In some embodiments, the anhydride is represented by the general formula (III):

(III)

In some embodiments, the anhydride is formed by reacting the bifunctional linker of general formula (I):

(I)

where $X_1$, $X_2$ and $R_1$, $R_2$, $R_3$, $R_5$ and W are as defined with for formula (I).

The conversion to the anhydride form requires reaction of the bifunctional compound of formula (I) with a coupling reagent (coupling reaction). In some embodiments, the coupling reagent is a carbodiimide. In some embodiments, the carbodiimide is selected from the group consisting of N,N'-diisopropylcarbodiimide (DIC), N,N'-Dicyclohexylcarbodiimide (DCC).

In some embodiments, the carbodiimide is N,N'-Dicyclohexylcarbodiimide (DCC).

The formation of BAPA anhydride is known in the art. In some embodiments, the formation of the anhydride requires a reaction period of several hours.

Figure 1B:
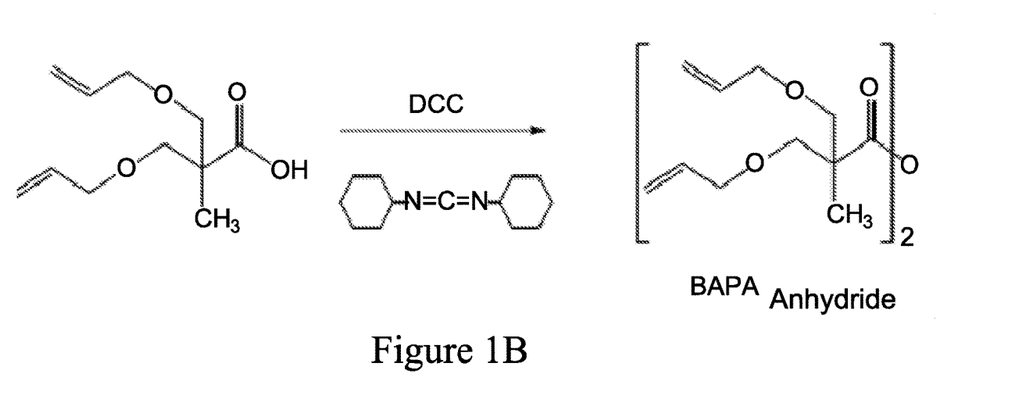
Figure 1C:
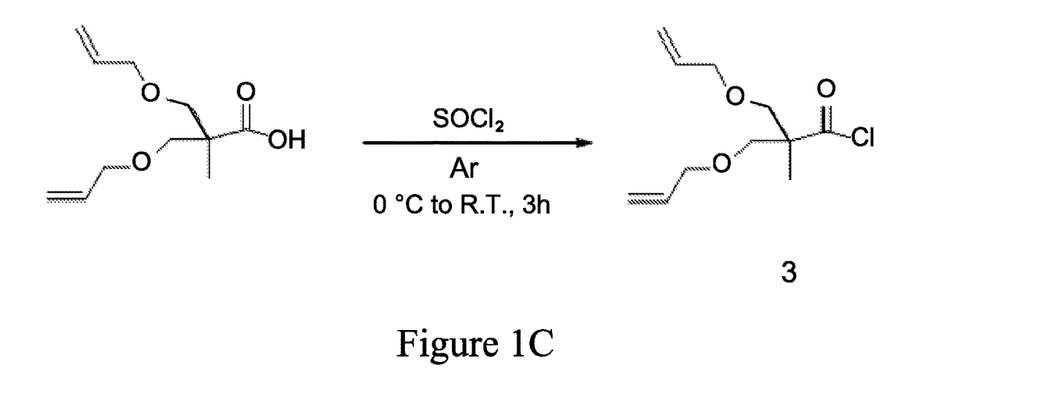

The conversion of BAPA to its anhydride form is known in the art and is also illustrated in FIGS. 1B, and 1C where BAPA is reacted with DCC to form BAPA anhydride.

The anhydride is then used for the modification of the surface of a polymer-containing matrix. This is achieved by exposing the surface of the matrix that contains the polar reactive groups, e.g. hydroxyl groups (as with cellulose fibers) to the anhydride.

The reaction conditions may vary, depending, inter alia, on the type of anhydride used.

In some embodiments, the reaction being carried out at room temperature (20-25° C.), in the presence of a reaction medium comprising a pyridine derivative in a polar aprotic solvent.

The pyridine derivative can be any one known in esterification and amidation. In some embodiments, the pyridine derivative is a dialkylaminopyridine.

In some embodiments, the pyridine derivative is 4-dimethylaminopyridine (DMAP).

In some embodiments, the polar aprotic solvent is selected from the group consisting of dimethyl sulfoxide (DMSO), dimethylformamide (DMF), dihalomethane. In some embodiments, the polar aprotic solvent is dichloromethane (DCM).

In some embodiments, the reaction medium comprises also an amine containing organic compound, such as, without being limited thereto, pyridine or pyridine derivative, dimethylaminopyridine (DMAP), and trimethylamine. In some embodiments, the amine containing compound is pyridine.

At time, the modification reaction takes place for a period of at least 1 hour, at times, for a period of at least 2, 3, 4, 5, hours.

The resulting modified polymer containing matrix comprises the polymers of the matrix having, covalently bound thereto, a plurality of the bifunctional linker defined herein.

As noted above, the binding of the linker to the surface is such that the $R_1$ and $R_2$ are left free for functionalization by a functional agent as illustrated below. Further illustrated below, in accordance with some embodiments, the binding of the linker to the surface is by the formation of an ester or ether linkage with the polymer chain.

Figure 2:
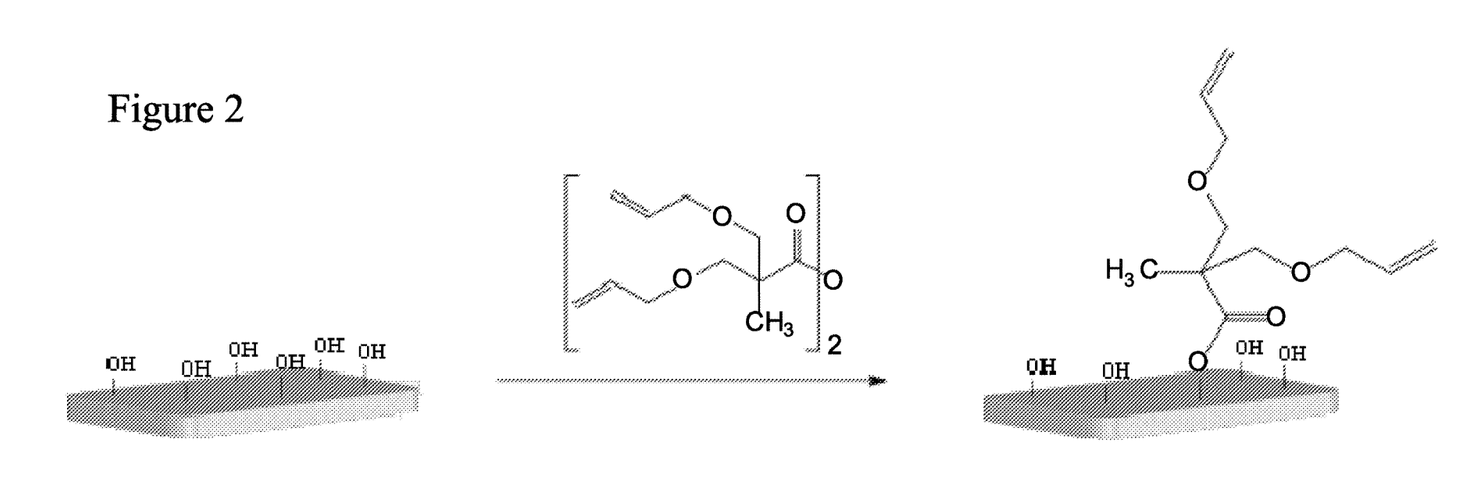
FIG. 2 is a schematic illustration of the surface modification of cellulose with molecular linker 2.

The modification of surface carrying hydroxyl reactive groups is illustrated in FIG. 2. Specifically, as illustrated, hydroxyl groups are reacted with BAP anhydride in the presence of DMAP and pyridine, both dissolved in DCM. The reaction is carried out, in this exemplary embodiment for 24 hours, at room temperature.

Once the modified surface is formed, it may then be reacted with any desirable functional agent to form a functionalized polymeric matrix. The functionalization of the modified surface was found to be an speedy reaction when the modified surface and the functional agent are exposed to UV light (in the presence of a radical initiator). As illustrated in the exemplary embodiment of FIG. 4, the modified surface, in this embodiment, BAPA modified surface, is brought into contact with the functional agent and by the aid of UV light, the functional agent is reacted with the allyl moieties of BAPA.

In some embodiments, functionalization is achieved using thermal energy (i.e. thermal initiation). For example, it has been found that when the functional agent is black or very dark colored, thermal activation of the reaction is preferable.

Radical initiators are known in the art as compounds that promote radical reactions (by facilitating the production of radical species). In some embodiments, the radical initiator is a substance selected from the group consisting of, without being limited thereto, 2,2-Dimethoxy-2-phenylacetophenone (DMPA) and 4,4'-Azobis(4-cyanovaleric acid).

In some embodiments, functionalization is achieved using thiols to generate repetitively branched molecules for example dendritic linker.

In some embodiments, the thiol is 2-Mercaptoethanol.

In some embodiments, functionalization is to provide a fluorescent marker, e.g. when the functional agent is a fluorescent compound.

In some embodiments, the functional agent comprises coumarin.

In some embodiments, the functional agent is a compound having electrical conductivity.

In some embodiments, a functional agent having electrical conductivity is one comprising polythiophene.

Figure 5:
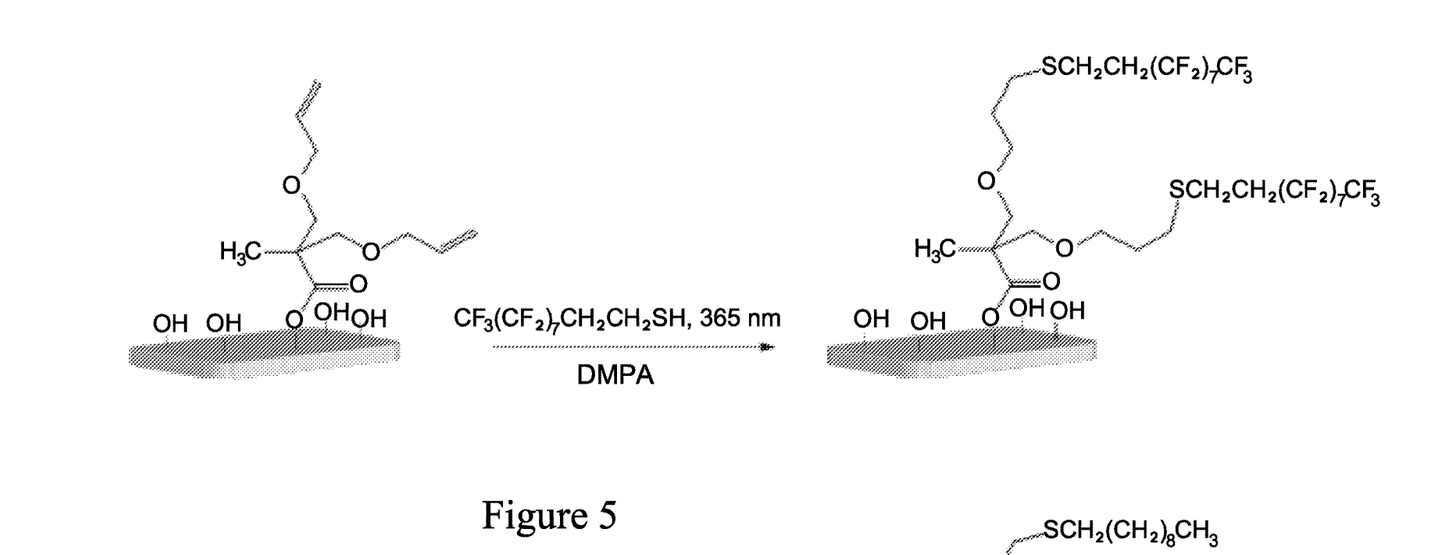
FIG. 5 is a schematic illustration of incorporation of 1H,1H,2H,2H-perfluorodecanethiol into linker-modified cellulose filter paper.

The formation of exemplary functionalized surfaces is illustrated in FIG. 5, which is further discussed below. In these two illustrated embodiments, the bifunctional linker is reacted by a thiol-ene click reaction. A thiol-ene click reaction is known in the art as a radical reaction which is initiated by a photochemical process (UV light) or by thermal initiation.

As used herein, the forms "a", "an" and "the" include singular as well as plural references unless the context clearly dictates otherwise. For example, the term "bifunctional linker" includes one or more such compounds.

Further, as used herein, the term "comprising" is intended to mean that the polymer containign matrix (for example) can include a polymer but not excluding other elements, such as non-polymeric material. The term "consisting essentially of" is used to define for example, matrices, which include polymers exclude other elements that may have an essential significance on properties of the matrix. "Consisting of" shall thus mean excluding more than trace elements of elements other than the polymers forming the matrix. Embodiments defined by each of these transition terms are within the scope of this invention.

Further, all numerical values, e.g. when referring the amounts or ranges approximations are also included, the values being varied (+) or (−) by up to 20%, at times by up to 10% of from the stated values. It is to be understood, even if not always explicitly stated that all numerical designations are preceded by the term "about".

The invention will now be exemplified in the following description of experiments that were carried out in accordance with the present disclosure. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

Non-Limiting Examples

Example 1: Preparation of Bis-Allyl Propionic Acid, BAPA and BAPA Anhydride and BAPA-acyl chloride Materials:

Cellulose filter paper (Whatman brand), was used as a cellulose substrate and was dried in a vacuum oven at 65° C. for 14 hours prior to use. 2,2-Bis(hydroxymethyl)propionic acid (Bis-MPA), allyl bromide, thionyl chloride ($SOCl_2$), N,N'-dicyclohexylcarbodiimide (DCC), pyridine, 4-dimethyl(aminopyridine) (DMAP) 1H,1H,2H,2H-perfluorodecanethiol, 1-decanethiol, 2-mercaptoethanol, 2,2-dimethoxy-2-phenyl-acetophenone (DMPA) were purchased from Sigma-Aldrich. Trimethylamine ($Et_3N$), toluene, dichloromethane (DCM), dry DCM and ethyl alcohol were purchased from Bio-lab ltd. Concentrated hydrochloric acid (HCl) and sodium hydroxide (NaOH) pellets were purchased from Merck. All the materials were used as received.

Experimental Procedure

Preparation of BAPA (Precursor for the Synthesis of the Molecular Linkers "2" and "3" Below).

Bis-MPA (20 gr, 0.15 mol) and NaOH (58 gr, 1.44 mol) were added to a two neck round bottom flask containing 300 mL of toluene. The reaction vessel was heated to 110° C. and the mixture was left about 30 min. under vigorous stirring. Then, allyl bromide (125 gr, 1.04 mol) was added to the vessel and the reaction mixture was refluxed overnight. After the reaction was completed, the mixture was acidified (pH ca. 1-2) concentrated HCl. The mixture was washed using 200 mL of water and then 200 mL of brine solution. The organic phase was dried with $MgSO_4$, followed by removal of the solvent under vacuum. The crude product was purified using column chromatography to give a slightly viscous and yellowish liquid (25.4 gr, 77%).

The synthesis of BAPA is also known in the art [Montanez, Maria I., et al. "Accelerated growth of dendrimers via thiolene and esterification reactions." Macromolecules 43.14 (2010): 6004-6013.]. Generally, the synthesis was carried out according the Scheme provided in FIG. 1A.

Preparation of Bis(Allyl Propionic Acid) Anhydride ("Linker 2").

BAPA (10 gr, 46.73 mmol) and DCC (4.82 gr, 23.36 mmol) were added to a round bottom flask containing 25 mL of DCM. The mixture was stirred overnight at room temperature. The DCC-urea by product was removed by vacuum filtration using glass filter, followed by removal of the solvent under vacuum. The product was isolated as a slightly viscous and yellowish liquid (8.33 gr, 87%).

Generally, the synthesis was carried out according the Scheme provided in FIG. 1B. A synthesis of BAPA anhydride is also known in the art (Malkoch, Michael, Eva Malmstrom, and Anders Hult. "Rapid and efficient synthesis of aliphatic ester dendrons and dendrimers." Macromolecules 35.22 (2002): 8307-8314.).

Preparation of Bis(Allyl Propionoyl Chloride) ("Linker 3").

Generally, the synthesis was carried out according the Scheme provided in FIG. 1C. Specifically, BAPA (2.5 g, 0.012 mol) was charged in a flame dried flask and cooled to 0° C. Next, $SOCl_2$ (10 mL, 0.14 mol) was added dropwise to the neat BAPA with stirring. Upon completion of the addition, the reaction was further stirred for 3 hours at room temperature, followed by evaporation of the excess $SOCl_2$ under reduced pressure. Product (3) in FIG. 1C was obtained quantitatively as a yellow oil and used without further purification. $^1$H NMR (400 MHz, $CDCl_3$): δ 5.86 (m, 2H), 5.27 (dq, J=17.2, 1.6 Hz, 2H), 5.18 (dq, J=10.5, 1.3 Hz, 2H), 4.00 (dt, J=5.5, 1.3 Hz, 4H), 3.60 (s, 4H), 1.34 (s, 3H) ppm; $^{13}$C NMR (100 MHz, $CDCl_3$): δ 176.5 (C), 134.4 (CH), 117.3 ($CH_2$), 72.5 ($CH_2$), 71.6 ($CH_2$), 58.5 (C), 18.1 ($CH_3$) ppm; Cold cluster CI-MS: m/z 233.2 $[M+H]^+$.

Example 2: Modification of Cellulose Filter Paper with Linker Molecule

Surface Modification of Cellulose Filter Paper with Molecular Linker 2.

Generally, the surface modification of the cellulose filter with the linker molecule was carried out according the Scheme provided in FIG. 2.

Specifically, filter paper (WHATMAN, number 4) (53.7 mg, 2×3 cm) was washed with acetone and then vacuum dried at 65° C. for 14 hours prior to use. Next, filter paper was immersed into a glass flask containing molecular linker 2 (2.5 gr, 6.1 mmol), DMAP (2.3 gr, 19 mmol) and pyridine (410 µl, 5 mmol) in DCM (8 mL). The reaction was carried out at room temperature for 24 hours using shaker, followed by soxhlet extraction with DCM for 24 hours to remove residual reactants. Subsequently, the filter paper was washed with deionized water, EtOH and finally washed again with DCM, followed by vacuum drying at 65° C. for 14 hours.
Surface Modification of Cellulose Filter Paper with Linker 3.

Figure 3:
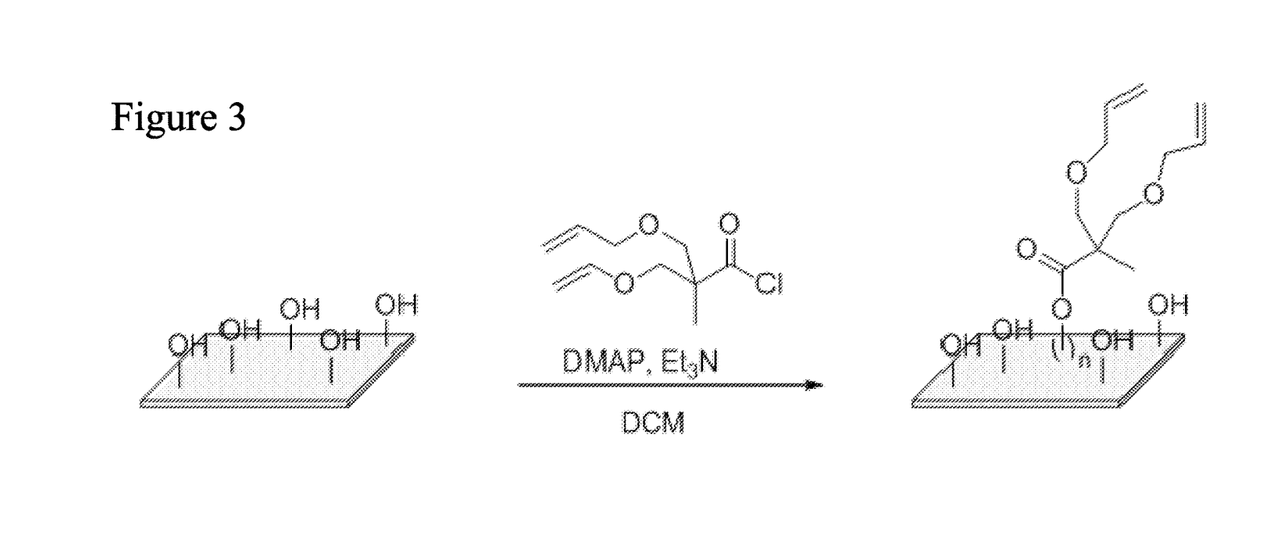
FIG. 3 is a schematic illustration of the surface modification of cellulose with molecular linker 3.

Generally, the modification of the cellulose filter paper with the linker was carried out according the Scheme provided in FIG. 3.

Specifically, filter paper (WHATMAN, number 4) (80.1 mg 3×3 cm) was washed with acetone and then vacuum dried at 65° C. for 14 hours prior to use. Next, filter paper was introduced into a flame-dried glass flask containing dry DCM (8 mL), DMAP (0.475 mmol, 58 mg) and $Et_3N$ (1.45 ml, 10.45 mmol). Next, a solution of the molecular linker 3 (2.2 gr, 9.5 mmol) in 4 ml of dry DCM was added to the flask and the reaction was stirred at 50° C. for 2 hours. Upon cooling to room temperature, the modified filter paper was extracted twice with DCM, washed with deionized water and EtOH and further extracted using soxhlet in DCM for 18 hours. Finally, the filter paper was dried at 65° C. for 14 hours.

Figure 4A:
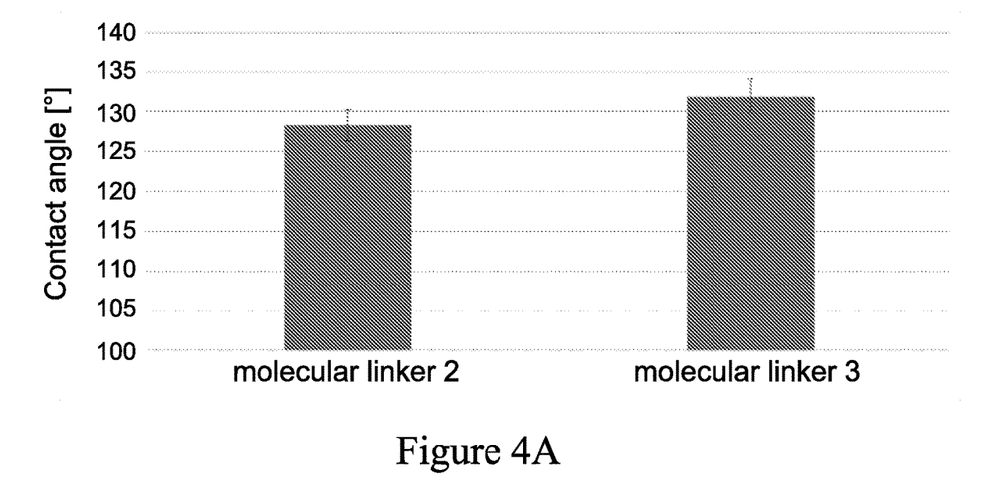
FIGS. 4A and 4B present contact angle measurements of cellulose filter paper modified with bis(allyl propionic acid) anhydride (linker 2) and bis(allyl propionoyl chloride (linker 3) (FIG. 4A) and the change in these contact angles in time (FIG. 4B).
Figure 4B:
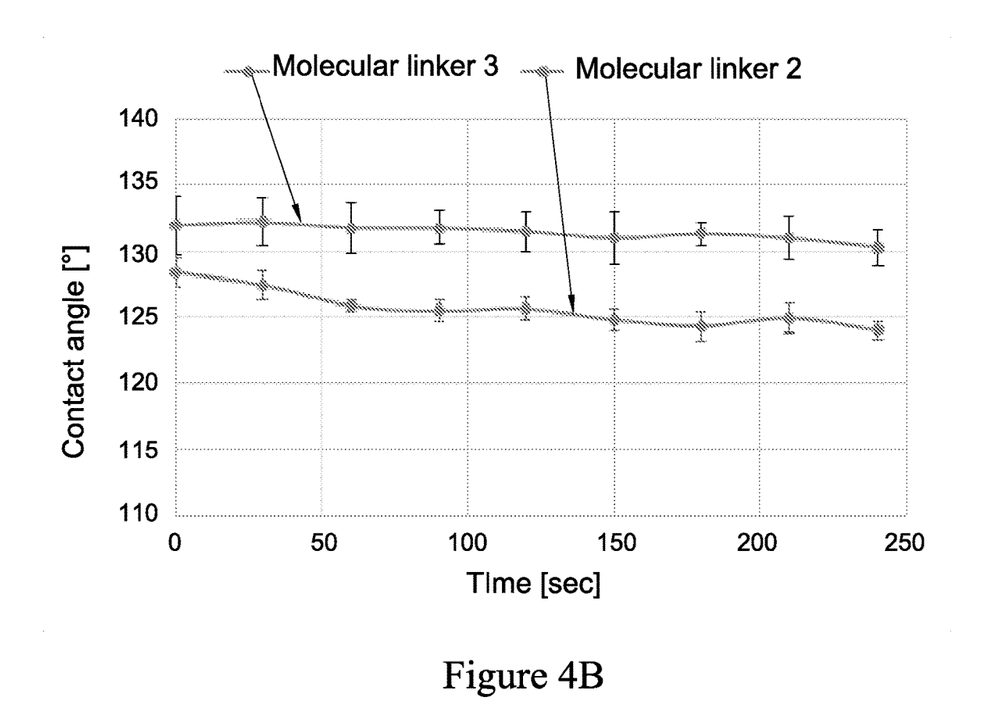

FIGS. 4A-4B, which are further discussed below, show that the modification with linker 2 or linker 3 both resulted in an increase in hydrophobicity of the surface.

Example 3: Characterization of Cellulose Filter Paper Modified with Molecular Linkers 2 and 3

Contact Angle Measurements.

The modifications describes in Example 2, with linker 2 and linker 3, resulted in an increase in hydrophobicity of the surface. This is evident from the contact angle measurements of cellulose filter paper modified with each molecular linker as shown in FIGS. 4A and 4B.

X-Ray Photoelectron Spectroscopy Measurements.

High-resolution X-ray Photoelectron Spectroscopy (XPS) analysis of the unmodified filter paper, filter paper modified with molecular linker 2 and filter paper modified with molecular linker 3 are presented in Table 1.

TABLE 1

| High-resolution X-ray Photoelectron Spectroscopy (XPS) analysis | | | |
| --- | --- | --- | --- |
| Sample | Unmodified paper | Linker 2- modified paper | Linker 3- modified paper |
| C1 intensity (C—C, C—H) | 18.1% | 24.2% | 26.2% |
| C2 intensity (C—O) | 63.2% | 54.8% | 56.9% |
| C3 intensity (O—C—O) | 17.3% | 15.9% | 13.8% |
| C4 intensity (O—C=O) | 1.4% | 5.0% | 3.1% |
| O/C ratio | 0.66 | 0.55 | 0.55 |

Example 4: Incorporation of Functional Materials into Linker-Modified Cellulose Filter Paper Procedure for Covalent Binding of 1H, 1H, 2H, 2H-Perfluorodecanethiol.

Generally, the incorporation was carried out according the synthetic route provided in FIG. 5.

Specifically, bis(allyl propionic acid) anhydride modified cellulose paper (36 mg, 1.6×2.5 cm) was placed into a solution containing 1H,1H,2H,2H-perfluorodecanethiol (0.5 gr, 1.04 mmol), DMPA (5 wt %) and 1 ml DCM. Next, the reaction vessel was sealed and purged with argon for 1 min. The reaction mixture was irradiated for 15 min. at 365 nm using UV lamp. This procedure was repeated for the other side of the filter paper. After the reaction was completed, the modified cellulose paper was extracted with DCM using soxhlet for 18 hours and dried in a vacuum oven at 65° C. for 14 hours.

Procedure for Covalent Binding of 1-Decanethiol.

Figure 6:
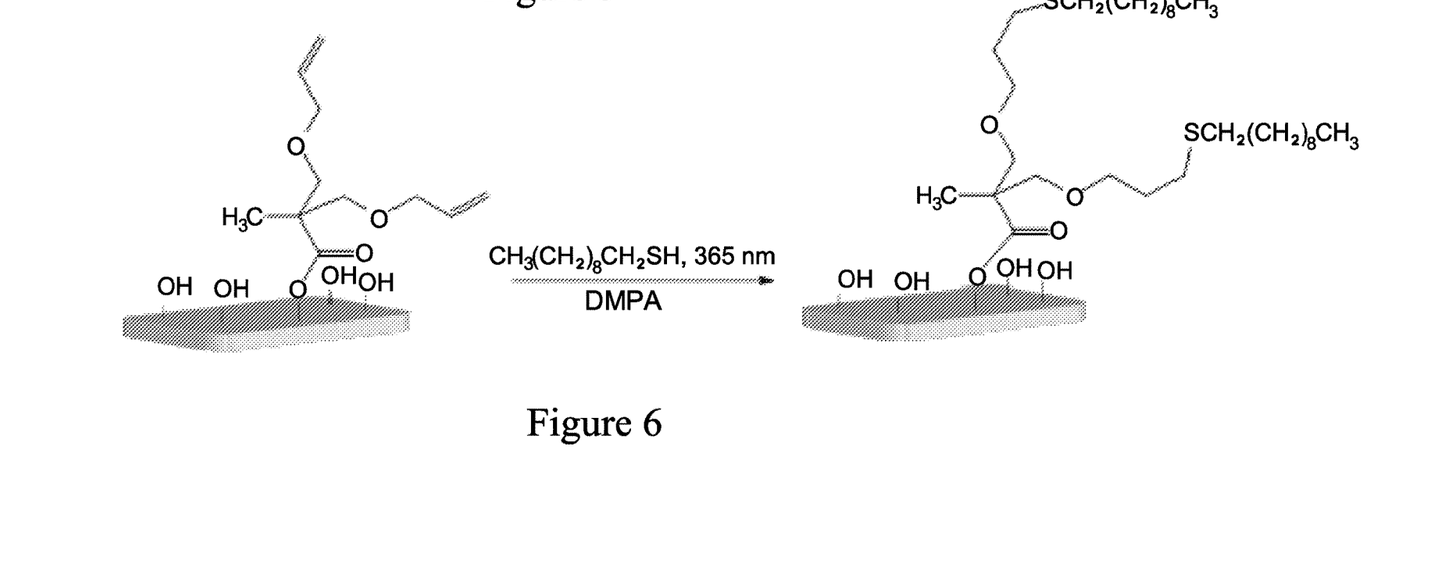
FIG. 6 is a schematic illustration of incorporation of 1-decanethiol into linker-modified cellulose filter paper.

Generally, the incorporation was carried out according the synthetic route provided in FIG. 6.

Specifically, bis(allyl propionic acid) anhydride modified cellulose paper (36 mg, 1.6×2.5 cm) was placed into a solution containing 1-decanethiol (0.5 gr, 2.87 mmol), DMPA (5 wt %) and 1 ml DCM. Next, the reaction vessel was sealed and purged with argon for 1 min. The reaction mixture was irradiated for 15 min. at 365 nm using UV lamp. This procedure was repeated for the other side of the filter paper. After the reaction was completed, the modified cellulose paper was extracted with DCM using soxhlet for 18 hours and dried in a vacuum oven at 65° C. for 14 hours.

Procedure for Covalent Binding of Mercaptoethanol.

Figure 7:
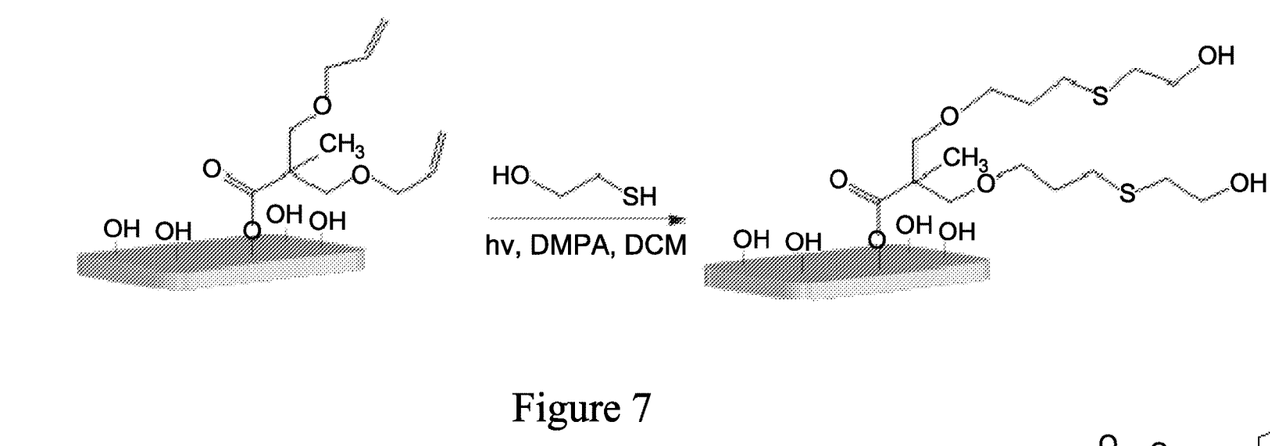
FIG. 7 is a schematic illustration of incorporation of mercaptoethanol into linker-modified cellulose filter paper.

Generally, the incorporation was carried out according the Scheme provided in FIG. 7.

Specifically, filter paper modified with molecular linker 2 (26.05 mg, 3×1 cm) was vacuum dried at 65° C. for 14 hours and then added to a solution containing 2-mercaptoethanol (1 gr, 12.8 mmol), DMPA (5 wt %) in 3 ml DCM. The reaction vessel was sealed and purged with argon for 1 min. and thereafter irradiated with a 365 nm UV lamp for 20 min. Subsequently, the filter paper was extracted with DCM via soxhlet to remove residual reactants and dried in a vacuum oven at 65° C. for 14 hours.

Figure 8:
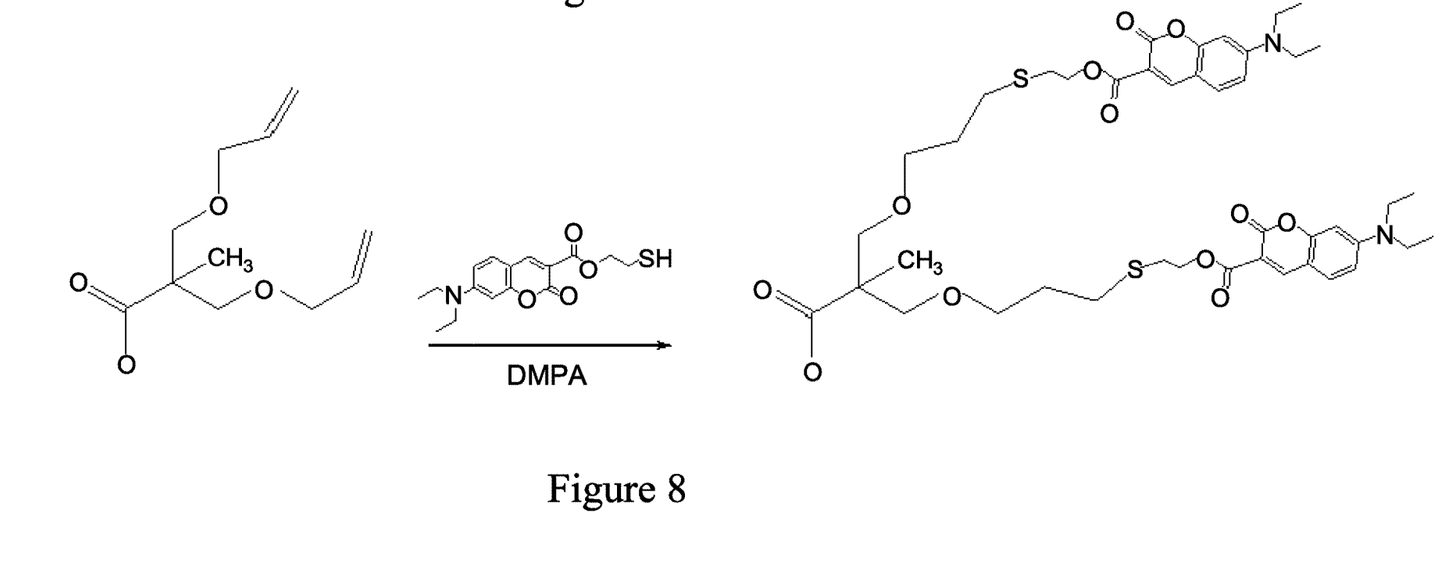
FIG. 8 is a schematic illustration of incorporation of coumarin-thiol into linker-modified cellulose filter paper.

Attachment of Coumarin-Thiol to the Filter Paper Modified with Linker Generally, the incorporation of a linker was carried out according the Scheme provided in FIG. 8.

A modified cellulose paper (18.45 mg, 1.5×1.2 cm) was placed into a solution containing DCM (800 µL), coumarin-thiol (30 mg, 0.093 mmol) and DMPA (5 wt %). The reaction vessel was sealed and purged with argon for 1 min., followed by irradiation with a 365 nm UV lamp for 20 min. Subsequently, the filter paper was extracted with DCM using soxhlet for 18 hours and dried in a vacuum oven at 65° C. for 14 hours. The reaction was also performed in a similar manner using the same molar amounts on unmodified cellulose paper as a control.

Example 5: Characterization of Linker-Modified Filter Paper Bonded to Functional Materials

Figure 9:
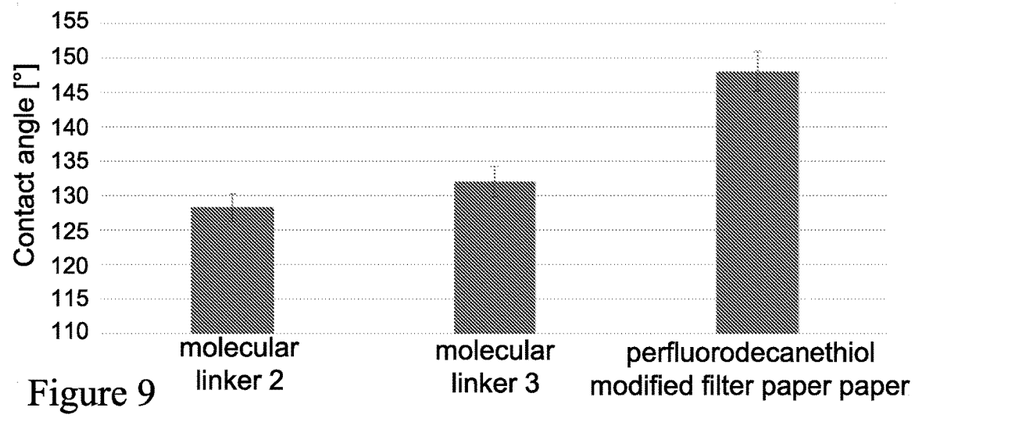
FIG. 9 presents contact angle measurements of the cellulose filter paper modified with molecular linkers 2, molecular linker 3 or perfluorodecanethiol.

The contact angle measurements of the cellulose filter paper modified with molecular linker 2, molecular linker 3 or perfluorodecanethiol are presented in FIG. 9. They show that the binding of the functional agent to the molecular linker increased the hydrophobicity of the linker-filter paper.

Figure 10:
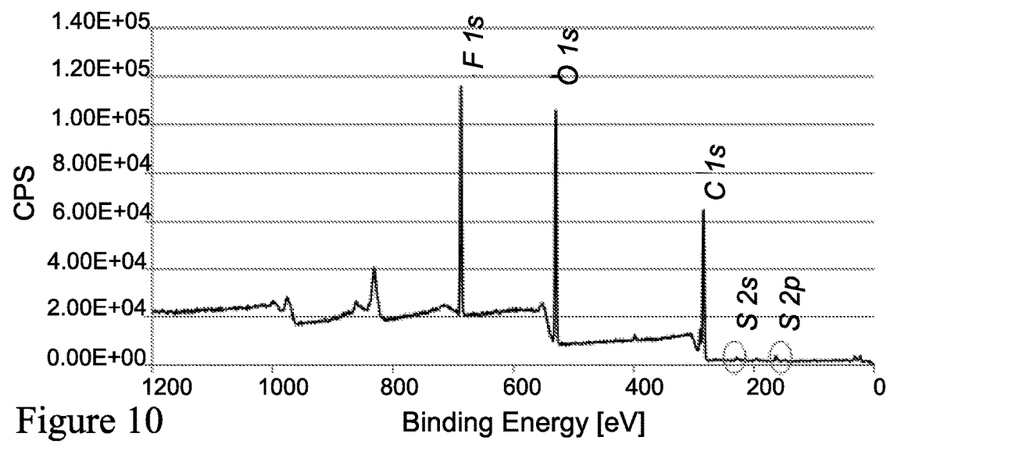
FIG. 10 is a graph showing the intensity (CPS) for low resolution XPS of perfluorodecanethiol modified filter paper.

Further, a low resolution XPS of perfluorodecanethiol-modified filter paper is presented in FIG. 10. This Figure confirms the binding of the perfluorodecanethiol functional agent to the filter paper.

Figure 11:
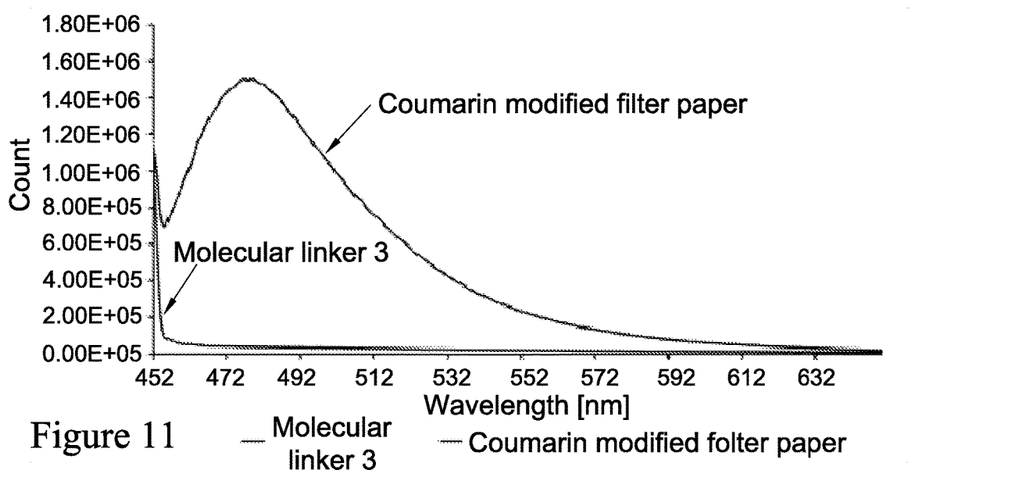
FIG. 11 is a graph showing the solid-state fluorescence measurements of the molecular linker 3 and coumarin-modified filter paper (excitation at 435 nm).

Further, solid-state fluorescence measurement of the molecular linker- and coumarin-modified filter paper (excitation at 435 nm) is presented in FIG. 11. This figure shows the fluorescence intensity of the functional agent on the modified filter paper as compared to the filter paper carrying only the linker, without the functional agent.

The invention claimed is:

1. A modified polymeric fabric comprising:
a polymeric fabric comprising cellulose; and
a plurality of bifunctional linkers of formula (I):

(I)

where:
R$_1$ and R$_2$ are each independently vinyl, alkyl vinyl, propargyl, alkyl propagyl, allenyl, or alkyl allenyl;
R$_3$ is an alkyl;
X$_1$ and X$_2$ are each independently —O—(CH$_2$)$_n$— or —S—(CH$_2$)$_n$—, where n is independently with respect to X$_1$ and X$_2$ an integer of 1 to 4;
W is an oxygen atom of the cellulose; and
R$_5$ is alkylene or carbonyl.

2. A functionalized polymer-containing fabric comprising:
a polymer-containing fabric comprising cellulose; and
at least one functional agent bound at a surface of the polymer-containing fabric via a bifunctional linker of formula (I):

(I)

where:
R$_1$ and R$_2$ are each independently vinyl, alkyl vinyl, propargyl, alkyl propagyl, allenyl, and alkyl allenyl;
R$_3$ is an alkyl;
X$_1$ and X$_2$ are each independently —O—(CH$_2$)$_n$ or —S—(CH$_2$)$_n$, where n is independently with respect to X$_1$ and X$_2$ an integer from 1 to 4;
R$_5$ is alkylene or carbonyl; and
W is an oxygen atom of the cellulose.

3. A modified cellulose-containing fabric comprising: cellulose fibers; and a bis-allyl propionic acid (BAPA) linker covalently bound to an oxygen atom of said cellulose fibers.

4. The modified cellulose-containing fabric of claim 3, further comprising a functional agent bound to said modified cellulose-containing fabric via said bis-allyl propionic acid (BAPA) linker.

5. A process for modifying a surface of a polymer-containing fabric, the process comprises:
providing a fabric comprising cellulose,
wherein the cellulose having, prior to being modified, exposed hydroxyl groups; and
reacting said fabric with a compound of formula (II):

(II)

where:
R$_1$ and R$_2$ are each independently vinyl, alkyl vinyl, propargyl, alkyl propagyl, allenyl, or alkyl allenyl;
R$_3$ is an alkyl;
R$_5$ is alkylene or carbonyl;
W' is O; and
X$_1$ and X$_2$ are each independently —O—(CH$_2$)$_n$— or —S—(CH$_2$)$_n$—, where n is independently with respect to X$_1$ and X$_2$ an integer of 1 to 4;
in the presence of a reaction medium comprising an amine-containing organic compound in a polar aprotic solvent, so as to form an ester linkage or an ether linkage that binds the compound of formula II to the fabric, wherein the ester linkage and the ether linkage are each a reaction product of W and at least one of the exposed hydroxyl groups of the cellulose.

6. The process of claim 5, wherein said amine-containing organic compound is 4-Dimethylaminopyridine (DMAP).

7. The process of claim 5, wherein said polar aprotic solvent is dichloromethane (DCM) and said reaction medium comprises pyridine.

8. The process of claim 5, wherein R$_1$ and R$_2$ each represent —CH$_2$—CH=CH$_2$.

9. The process of claim 5, wherein R$_3$ represents a methyl.

10. The process of claim 5, wherein X$_1$ represents —O—CH$_2$—.

11. The process of claim 5, wherein X$_2$ represents —O—CH$_2$—.

12. The process of claim 5, wherein R$_5$ represents a carbonyl.

* * * * *